United States Patent [19]

Bresson et al.

[11] Patent Number: 4,482,480

[45] Date of Patent: Nov. 13, 1984

[54] POLYCARBOXYLIC ACID DERIVATIVES AND USES

[75] Inventors: Clarence R. Bresson; Robert M. Parlman; Benjamin R. Robles, all of Bartlesville, Okla.

[73] Assignee: Phillips Petroleum Company, Bartlesville, Okla.

[21] Appl. No.: 480,206

[22] Filed: Mar. 30, 1983

[51] Int. Cl.$^3$ .......................... C09K 3/00; C22B 1/00; C22B 3/00

[52] U.S. Cl. .................................... 252/61; 260/455 B

[58] Field of Search ...................... 252/61; 260/455 B

[56] References Cited

U.S. PATENT DOCUMENTS

| | | | |
|---|---|---|---|
| 1,833,740 | 11/1931 | Derby et al. | 252/61 |
| 2,449,984 | 9/1948 | Gibbs | 209/167 |
| 3,464,899 | 9/1969 | Chessin et al. | 204/29 |
| 3,796,645 | 3/1974 | Fujita et al. | 204/141.5 |
| 4,329,223 | 5/1982 | Ramadorai et al. | 209/167 |
| 4,425,230 | 1/1984 | Andress et al. | 252/61 |

OTHER PUBLICATIONS

30891 U.S. Ser. No. 387,393, filed 6-11-82, now abandoned.
31287 U.S. Ser. No. 489,846, filed 5-6-83, Bresson et al.
31075 U.S. Ser. No. 436,883, filed 10-26-82, Parlman et al.

*Primary Examiner*—Paul Lieberman
*Assistant Examiner*—Robert A. Wax

[57] ABSTRACT

Mercapto polycarboxylic acids, especially the trithiocarbonate derivatives thereof and alkali metal salts, are employed as treating agents in mineral recovery operations.

9 Claims, No Drawings

POLYCARBOXYLIC ACID DERIVATIVES AND USES

BACKGROUND OF THE INVENTION

The present invention relates to a composition of matter. In another aspect, the invention relates to a depressant composition useful in ore flotation operations. Another aspect of this invention relates to a process for recovering minerals from ore compositions. Yet a further aspect of this invention relates to a process for preparing a composition of matter.

Flotation processes are known in the art and are used for recovering and concentrating minerals from ores. In froth flotation processes the ore is crushed and wet ground to obtain a pulp. Additives such as mineral flotation or collecting agents, frothers, suppressants, stabilizers, etc. are added to the pulp to assist separating valuable materials from undesirable or gangue portions of the ore in subsequent flotation steps. The pulp is then aerated to produce a froth at the surface. The minerals which adhere to the bubbles or froth are skimmed or otherwise removed and the mineral bearing froth is collected and further processed to obtain the desired minerals. Typical mineral flotation collectors include xanthates, amines, alkyl sulfates, arene sulfonates, dithiocarbamates, dithiophosphates, and thiols.

While the art of ore flotation has reached a significant degree of sophistication it is a continuing goal in the ore flotation industry to increase the productivity of ore flotation processes and above all to provide specific processes which are selective to one ore or to one metal over other ores or other metals, respectively, which are present in the material to be treated.

OBJECTS OF THE INVENTION

It is one object of this invention to provide a composition useful in ore flotation processes.

Another object of this invention is to provide a process to produce such a composition.

Yet a further object of this invention is to provide an improved flotation process using the new depressant composition.

A still further object of this invention is to provide an improved molybdenum flotation process in which less iron, copper and lead is present in the molybdenum values recovered.

These and other objects, advantages, details, features and embodiments of this invention will become apparent to those skilled in the art from the following detailed description of the invention and the appended claims.

SUMMARY OF THE INVENTION

In one aspect, the invention relates to a composition which comprises an ammonium or Group IA metal salt of the trithiocarbonate derivative of a mercapto polycarboxylic acid, said salt being represented by the formula:

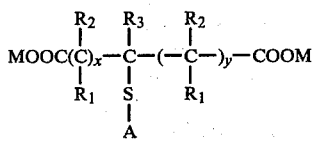

where M represents ammonium or Group IA metal and A represents

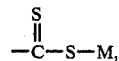

$R_1$ and $R_2$ are selected from the group consisting of hydrogen and an alkyl group having 1 to 3 carbon atoms, $R_3$ is selected from the group consisting of hydrogen, alkyl group having 1 to 3 carbon atoms, and COOM and x and y are 0 or an integer of 1 through about 7.

In another aspect, a composition is prepared by reacting an ammonium or Group IA metal salt of a mercapto polycarboxylic acid which can be represented by the above formula where A equals M, with carbon disulfide, $CS_2$. The ammonium or Group IA metal salt of the mercapto polycarboxylic acid can be prepared by neutralizing a mercapto polycarboxylic acid which can be represented by the above formula where A and M are both hydrogen with ammonium hydroxide or alkali metal hydroxide.

In yet another aspect of the invention, it has been found that compositions represented by the formula:

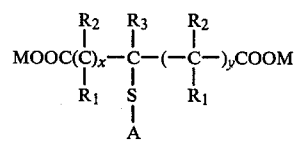

where M represents hydrogen, ammonium or Group IA metal, A represents hydrogen, ammonium, Group IA metal, or

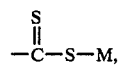

$R_1$ and $R_2$ are selected from the group consisting of hydrogen, alkyl group having 1 to 3 carbon atoms; $R_3$ is selected from the group consisting of hydrogen, alkyl group having 1 to 3 carbon atoms and COOM; and x and y are 0 or an integer of 1 through about 7, are usefully employed as treating agents in a minerals recovery operation, especially a molybdenum flotation operation.

DETAILED DESCRIPTION OF THE INVENTION

The composition of matter of the present invention comprises an ammonium or Group IA metal salt of the trithiocarbonate derivative of a mercapto polycarboxylic acid, preferably a dicarboxylic acid. This salt can be represented by the formula:

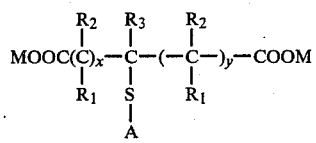

where M represents ammonium or Group IA metal, and A represents

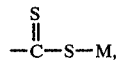

$R_1$ and $R_2$ are selected from the group consisting of hydrogen and an alkyl group having 1 to 3 carbon atoms, $R_3$ is selected from the group consisting of hydrogen, alkyl group having 1 to 3 carbon atoms, and and COOM, and x and y are 0 or an integer of 1 through about 7. Suitable Group IA metals for forming the salt are alkali metals, such as lithium, soidum, potassium, rubidium, and cesium. Sodium is the preferable Group IA alkali metal with which to form the salt.

The above described compositions can be prepared by reacting an ammonium or Group IA metal salt of a mercapto polycarboxylic acid which can be represented by the above formula except that A is M, with carbon disulfide, $CS_2$. The ammonium or Group IA metal salt of the mercapto polycarboxylic acid can be prepared by neutralizing a mercapto polycarboxylic acid which can be represented by the above formula except that A and M are hydrogen with ammonium hyroxide or alkali metal hyroxide. Suitable mercapto polycarboxylic acid starting materials are mercaptomalonic acid, 2-mercaptoglutaric acid, 2-mercaptosebacic acid, mercaptosuccinic acid, 3-mercaptoadipic acid, 3-mercaptocitric acid and combinations of these. Of these, mercaptosuccinic acid is the preferred starting material since it is commercially available and has been used with good results. Generally, aqueous sodium hydroxide is employed to neutralize the mercapto carboxylic acid. To the neutralized solution, the carbon disulfide is added in an amount sufficient to result in the treating agent.

The aqueous treating agent thus obtained is the preferred treating agent of the invention for use as a depressant composition in a flotation process.

Generally, the flotation process comprises carrying out a minerals flotation with a depressant composition present, with the depressant composition being represented by the formula:

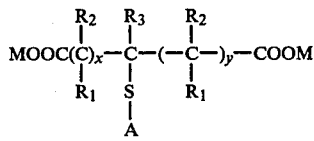

where M represents hydrogen, ammonium, or Group IA metal, A represents hydrogen, ammonium, Group IA metal,

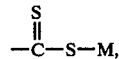

$R_1$ and $R_2$ are selected from the group consisting of hydrogen, alkyl group having 1 to 3 carbon atoms; $R_3$ is selected from the group consisting of hydrogen, alkyl group having 1 to 3 carbon atoms, and COOM; and x and y are 0 or an integer of 1 through about 7. Preferably, A is represented by the formula

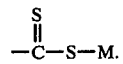

More preferably, A is represented by the formula

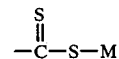

and M is sodium. Even more preferably, the compositions represented by the above formula have been derived from mercaptomalonic acid, 2-mercaptoglutaric acid, 2-mercaptosebacic acid, mercaptosuccinic acid, 3-mercaptoadipic acid, or 3-mercaptocitric acid.

Generally, the flotation process will utilize a composition comprising the mercapto polycarboxylic acid or derivative, water, and the mineral material. The depressants of the present invention can be used to depress iron, copper and/or lead in the presence of molybdenum. Usually the metals are in solid sulfided form and form a slurry, which can be finely divided, as in a pulp. For example, the invention can be employed to process an ore slurry containing high copper values. The invention can also be employed to process a concentrate, such as a concentrate which contains high molybdenum values. Generally, the solids to be processed will be present as a slurry in water which contains the mercapto polycarboxylic acid or derivative with the mercapto polycarboxylic acid or derivative being present in an amount of between about 0.005 and about 20 pounds per ton of the solids. The slurry usually contains between about 10 and 75 weight percent solids preferably in the range of 15–60 weight percent solids, depending on the processing stage. Preferably, the mercapto polycarboxylic acid or derivative is present in the composition in an amount in the range of between about 0.01 to about 6 pounds per ton of solids. Even more preferably, the mercapto polycarboxylic acid or derivative is present in an amount in the range of between about 0.5 and about 4 pounds per ton of the solids.

The flotation process usually involves the steps of:
(a) mixing crushed or ground mineral material with water and the depressant defined above to establish a pulp,
(b) aerating the pulp to produce a froth and a pulp,
(c) separating the froth from the pulp and producing a concentrate product and a tail product,
(d) recovering minerals from the so separated concentrate and/or tail product.

The suppressant composition of the invention can also be employed with frothers and flotation agents.

Examples of frothers that can be used in addition to the collector compositions defined above are polyoxyalkylene glycols and their corresponding methyl or ethyl ethers having broadly a molecular weight of about 400 to about 1000, and preferably a molecular weight in the range of about 420 to about 780. Particularly polypropylene glycols and their ethers having molecular weights of e.g., 400, 425, 750, or 900 can be used. Also polybutylene glycol and polypentylene glycol are useful materials. Examples of other frothers that may be used are alcohols such as methyl isobutyl carbinol, pine oil, phenols, fatty acids and cresylic acid. Examples of suitable flotation agents are organic xanthates, organic trithiocarbonates, amines, dithiocarbamates, fuel oils, aromatic oils and the like, generally in an amount of 0.005–0.5 pounds per ton of solids. Preferably frother and an oily flotation agent are used together.

The inventive suppressants can be used together with other suppressants or suppression steps if desired. For example, the suppressant composition defined above can be used after a surface treatment of the solids, such as after heating or oxidation of a concentrate or with sulfuric acid, and/or with additional suppressants, such as sodium cyanide, sodium ferrocyanide, lime and zinc sulfate, in the treatment of an ore.

The present invention is applicable to a variety of ores. The invention is particularly suitable for sulfided ores. Among the sulfided ores the molybdenum bearing ores and especially the molybdenum bearing ores which also contain copper, iron, or lead impurities, especially impurities of these metals in the sulfided form, are preferred. Examples of molybdenum bearing ores which are usefully processed with this invention are

| | |
|---|---|
| Molybdenite | $MoS_2$ |
| Wulfenite | $PbMoO_4$ |
| Porwellite | $Ca(Mo,W)O_4$ |
| Ferrimolybdite | $Fe_2Mo_3O_{12}\cdot 8H_2O$ |

Examples of copper ores which can be processed using inventive compositions, and/or which yield concentrates which can be processed using inventive compositions include

| | |
|---|---|
| Chalcocite | $Cu_2S$ |
| Chalcopyrite | $CuFeS_2$ |
| Covallite | $CuS$ |
| Bornite | $Cu_5FeS_4$ |
| Cubanite | $Cu_2SFE_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_3SbS_2$ |
| Tennanite | $Cu_{12}As_4S_{13}$ |

The following examples further illustrate preferred embodiments of this invention.

EXAMPLE I

This example describes the preparation of inventive collectors namely, disodium mercaptosuccinate and trisodium succinyl trithiocarbonate. To a 3-neck glass flask fitted wih a condenser, stirrer, thermometer and dropping funnel was added 125 milliliters of water and 42 grams (1.05 moles) of sodium hydroxide. After cooling to below 50° C., 50 grams (0.33 mole) of mercaptosuccinic acid was slowly added with stirring over a 20 minute period. The mixture was cooled to below 45° C. whereupon 25.4 grams (0.333 mole) of carbon disulfide was slowly added over a 30 minute period. The cloudy mixture was maintained with stirring at 45° C. for about 1.5 hours and the solution became clear and orange-colored. The solution was cooled to room temperature and bottled. The solution was calculated to be 40 weight percent of trisodium succinyl trithiocarbonate. The disodium salt of mercaptosuccinic acid solution disclosed herein was comprised of 1 gram of the free acid, 5 milliliters of 5 weight percent NaOH and 94 milliliters of $H_2O$.

EXAMPLE II

This example discloses the use of mercaptosuccinic acid derivatives described in Example I as ore flotation reagents, particularly as a Cu, Fe and Pb suppressant in a Mo ore flotation process. To a ball mill was charged 2010 grams of a Mo-bearing ore from Cyprus-Thompson Creek Mines along with 1000 milliliters of water, 0.5 g (0.5 lb/ton) lime and 5 milliliters (0.05 lb/ton) of a 1 weight percent aqueous solution of disodium mercaptosuccinate. Also added was 0.2 lb/ton (31 drops) of a fuel oil. The mixture was ground for 27.5 minutes, transferred to a Denver D-12 flotation cell along with enough water to come within 1 inch of the cell lip (approximately 30 percent solids). Also added to the cell was 15 drops (0.08 lb/ton) of a frother, MIBC (methyl isobutyl carbinol) and enough lime to adjust the pH to 8.9. The slurry was conditioned for 1 minute at 1500 rpm and floated for 1 minute. The rougher concentrate was filtered, dried analyzed. The run was repeated whereupon the average weight percent recovery of Mo, Cu, Fe and Pb was respectively 97.5%, 36.7%, 2.4% and 9.0%.

Several controls were then evaluated and the results compared with the inventive runs (No. 5). These results are all listed in Table I where it can be seen that the disodium mercaptosuccinate is a better suppressant (gives a lower % recovery) of Cu, Fe and Pb than any of the controls, Runs 1, 2, 3 and 4. Runs 2 and 3 employed similar compounds to the inventive compound except they were based on a monocarboxylic acid thio derivative rather than a dicarboxylic acid thio derivative. Likewise, Runs 1 and 2 are suppressants which did not perform as effectively as a Cu, Fe or Pb suppressant as the inventive run. The inventive suppressant continued to give about the same Mo recovery as the controls.

EXAMPLE III

This example discloses the effectiveness of both disodium mercaptosuccinate and trisodium succinyl trithiocarbonate as a Cu and Fe suppressant in a Cu ore concentrate. The general flotation process described in Example II was again followed but this time a Cu ore concentrate (Anamax Mines) was used instead of the ore itself, thus, no grind stage was carried out. The concentrate, about 415 milliliters (600 grams solids) of pulp (69 wt. % solids) was added to a 3-Liter Agitar LA500 flotation cell. After the suppressant was added and conditioned for 1-2 minutes the mineral was floated for 5 minutes at 200 rpm at a natural pH of 10.4. The new concentrate was filtered, dried and analyzed. The run was again repeated but the pH was adjusted to 6.4 with concentrated $H_2SO_4$ before floating. These results of both the inventive runs and controls are listed in Table II where it can be seen that the inventive suppressants, Runs 4 and 5, result in low recoveries of Fe and Cu while maintaining higher recoveries of Mo, hence, a higher purity of Mo is obtained with these suppressants as compared with the controls, Runs 1, 2 and 3. The two inventive suppressants, Runs 4 and 5, operate at both acidic and basic conditions giving low Cu and Fe recoveries while maintaining high Mo recoveries. Of the two inventive materials, trisodium succinyl trithiocarbonate appears to give the best Fe and Cu suppressant values.

TABLE I

Effect of Mercaptoalkanoic Acids as Cu, Fe, Pb Suppressants in a Mo Ore Flotation Process
2010 grams Ore (Cyprus-Thompson Creek)

| Run No. | Reagent[a] | Rougher Concentrate, Total Wt. g | Wt. % of Recovery | | | |
|---|---|---|---|---|---|---|
| | | | Mo | Cu | Fe | Pb |
| Control: | | | | | | |
| 1 | $Na_2SO_3$ | 0.25 lb/T | 17.9 | 98.1 | 59.7 | 4.33 | 26.5 |

TABLE I-continued

Effect of Mercaptoalkanoic Acids as
Cu, Fe, Pb Suppressants in a Mo Ore Flotation Process
2010 grams Ore (Cyprus-Thompson Creek)

| Run No. | Reagent[a] | | Rougher Concentrate, Total Wt. g | Wt. % of Recovery | | | |
|---|---|---|---|---|---|---|---|
| | | | | Mo | Cu | Fe | Pb |
| | | | 17.6 | 98.0 | 50.9 | 2.68 | 28.3 |
| 2 | Sodium Thioglycolate | 0.50 lb/T | Average = 20.2 | 98.1 | 55.3 | 3.51 | 27.40 |
| | | | 18.0 | 97.3 | 46.7 | 2.91 | 32.9 |
| | | | | 97.6 | 43.0 | 2.74 | 6.14 |
| 3 | Sodium Thiolactate | 0.50 lb/T | Average = 22.3 | 97.5 | 44.9 | 2.83 | 19.52 |
| | | | 19.6 | 98.1 | 50.6 | 3.24 | 32.3 |
| | | | | 97.2 | 47.7 | 2.67 | 27.0 |
| 4 | Disodium Carboxymethyl Trithiocarbonate,[b] | 0.50 lb/T | Average = 16.7 | 97.7 | 49.2 | 3.00 | 29.7 |
| | | | 19.7 | 97.7 | 55.6 | 3.12 | 31.6 |
| | | | | 97.9 | 54.8 | 3.34 | 31.6 |
| | | | Average = | 97.8 | 55.2 | 3.23 | 31.6 |
| Invention: | | | | | | | |
| 5 | Disodium Mercapto-Succinate | 0.50 lb/T | 17.3 | 97.3 | 32.1 | 2.47 | 13.5 |
| | | | 18.7 | 97.7 | 41.3 | 2.42 | 4.52 |
| | | | Average = | 97.5 | 36.7 | 2.44 | 9.01 |

[a] 1 wt. % Aq. Solution
[b] Available from Phillips Petroleum Co., ORFOM D-8

TABLE II

Effect of Mercapto Succinic Acid Salts as
Suppressants in a Mo Flotation Process
415 mL (600 g solids) Cu Ore Concentrate (Anamax Mines)

| Run No. | Suppressant - lb/Ton | pH 6.4 | | | | pH 10.4 | | | |
|---|---|---|---|---|---|---|---|---|---|
| | | Concentrate, Wt., g | Wt. % Recovery | | | Concentrate, Wt., g | Wt. % Recovery | | |
| | | | Cu | Fe | Mo | | Cu | Fe | Mo |
| Control: | | | | | | | | | |
| 1 | None | — | 33.9 | 5.1 | 4.3 | 82.5 | 142 | 25.7 | 25.7 | 27.8 |
| 2 | Molyflo[a] | 0.14 | 41.3 | 6.3 | 5.3 | 84.8 | 165 | 28.5 | 28.2 | 32.7 |
| 3 | Disodium Carboxymethyl Trithiocarbonate[b] | 0.8 | 25.0 | 3.0 | 4.0 | 6.3 | 26.2 | 3.4 | 4.0 | 57.9 |
| Invention: | | | | | | | | | | |
| 4 | Disodium Mercaptosuccinate | 0.8 | 35.8 | 5.1 | 4.3 | 75.8 | 86.6 | 16.6 | 13.1 | 66.9 |
| 5 | Trisodium Succinyl Trithiocarbonate | 0.8 | 24.3 | 2.8 | 3.3 | 78.5 | 24.9 | 3.0 | 3.2 | 72.1 |

[a] A Mo collector based on a hydrocarbon oil, available from Phillips Petroleum Co.
[b] A suppressant, ORFOM D-8, available from Phillips Petroleum Co.

What is claimed is:

1. A composition comprising a mercapto polycarboxylic acid derivative represented by the formula:

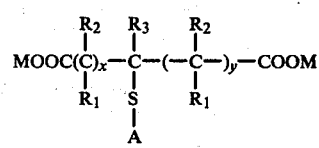

where $R_1$ and $R_2$ are selected from the group consisting of H and an alkyl group having 1 to 3 carbon atoms, $R_3$ is selected from the group consisting of hydrogen, alkyl group having 1 to 3 carbon atoms, and COOM, M is selected from the group consisting of ammonium, Li, Na, K, Rb and Cs, A represents

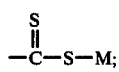

and x and y are 0 or any integer from 1 through 7.

2. A composition as in claim 1 further comprising an aqueous slurry of a solids-containing mineral material.

3. A composition as in claim 2 wherein the slurry contains between about 10 and about 75 weight percent solids and the mercapto polycarboxylic acid derivative is present in an amount of between about 0.005 and about 10 pounds per ton of solids.

4. A composition as in claim 3 wherein the mercapto polycarboxylic acid derivative is a derivative of a mercaptopolycarboxylic acid selected from the group consisting of mercaptomalonic acid, 2-mercaptoglutaric acid, 2-mercaptosebacic acid, mercaptosuccinic acid, 3-mercaptoadipic acid, and 3-mercaptocitric acid.

5. A composition as in claim 4 wherein the mercapto polycarboxylic acid derivative is present in an amount in the range of between about 0.05 and about 10 pounds per ton of solids.

6. A composition as in claim 5 containing 15–60 weight percent solids wherein the solids comprise molybdenum sulfide.

7. A composition as in claim 6 wherein the mercapto polycarboxylic acid derivative comprises an ammonium or Group IA metal salt of the trithiocarbonate derivative of mercaptosuccinic acid.

8. An aqueous composition suitable for use as a treating agent in an ore flotation process, said treating agent made by a process comprising:

(a) reacting ammonium hydroxide or an alkali metal hydroxide with a mercapto polycarboxylic acid represented by the formula

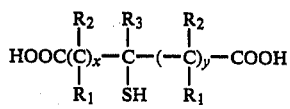

where $R_1$ and $R_2$ are independently selected from the group consisting of H and an alkyl group having 1 to 3 carbon atoms, $R_3$ is selected from the group consisting of H, alkyl group having 1 to 3 carbon atoms, and COOH, and x and y are 0 or an integer of 1 through 7, to form a reaction product; and (b) adding to the reaction product carbon disulfide in an amount sufficient to effect formation of the treating agent.

9. An aqueous composition as in claim 8 wherein sodium hydroxide is reacted with mercapto succinic acid to form the reaction product.

* * * * *